(12) United States Patent
Niu et al.

(10) Patent No.: US 7,834,246 B2
(45) Date of Patent: Nov. 16, 2010

(54) ROOT-PREFERRED REGULATORY ELEMENTS

(75) Inventors: Xiaomu Niu, Johnston, IA (US); Bruce Drummond, Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 48 days.

(21) Appl. No.: 12/183,515

(22) Filed: Jul. 31, 2008

(65) Prior Publication Data

US 2009/0106859 A1 Apr. 23, 2009

Related U.S. Application Data

(60) Provisional application No. 60/952,905, filed on Jul. 31, 2007.

(51) Int. Cl.
*A01H 1/00* (2006.01)
*C07H 21/04* (2006.01)
*C12N 15/00* (2006.01)
*C07K 14/415* (2006.01)

(52) U.S. Cl. .................... 800/295; 435/6; 435/69.1; 435/468; 435/419; 435/252.3; 435/320.1; 530/370; 536/24.1; 800/278; 800/287

(58) Field of Classification Search ............... 435/6, 435/69.1, 468, 419, 320.1; 536/24.1; 800/278, 800/295; 530/370
See application file for complete search history.

(56) References Cited

U.S. PATENT DOCUMENTS

2005/0155114 A1* 7/2005 Hinchey ............... 800/288

OTHER PUBLICATIONS

Xie, M., et al.; "Bidirectionalization of polar promoters in plants"; Nature Biotechnology (Jul. 2001) 19:677-679; MacMillan Publishers Ltd., US.

* cited by examiner

*Primary Examiner*—Phuong T Bui

(57) ABSTRACT

The present invention provides compositions and methods for regulating expression of heterologous nucleotide sequences in a plant. Compositions are novel nucleotide sequences for a root-preferred promoter and terminator isolated from the maize 6PGD coding region. A method for expressing a heterologous nucleotide sequence in a plant using the regulatory sequences disclosed herein is provided. The method comprises transforming a plant cell to comprise a heterologous nucleotide sequence operably linked to one or more of the regulatory sequences of the present invention and regenerating a stably transformed plant from the transformed plant cell.

12 Claims, 3 Drawing Sheets

ROOT-PREFERRED REGULATORY ELEMENTS

CROSS REFERENCE

This utility application claims the benefit U.S. Provisional Application No. 60/952,905, filed Jul. 31, 2007, which is incorporated herein by reference.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of operably linked regulatory elements that are functional within the plant host. Choice of the regulatory element will determine when and where within the organism the heterologous DNA sequence is expressed. Where continuous expression is desired throughout the cells of a plant, and/or throughout development, constitutive promoters are utilized. In contrast, where gene expression in response to a stimulus is desired, inducible promoters are the regulatory element of choice. Where expression in specific tissues or organs are desired, tissue-specific promoters may be used. That is, they may drive expression in specific tissues or organs. Such tissue-specific promoters may be temporally constitutive or inducible. In either case, additional regulatory sequences upstream and/or downstream from a core promoter sequence may be included in expression constructs of transformation vectors to bring about varying levels of expression of heterologous nucleotide sequences in a transgenic plant.

As this field develops and more genes become accessible, a greater need exists for transformed plants with multiple genes. These multiple exogenous genes typically need to be controlled by separate regulatory sequences however. Further, some genes should be regulated constitutively whereas other genes should be expressed at certain developmental stages or locations in the transgenic organism. Accordingly, a variety of regulatory sequences having diverse effects is needed.

Diverse regulatory sequences are also needed as undesirable biochemical interactions can result from using the same regulatory sequence to control more than one gene. For example, transformation with multiple copies of a regulatory element may cause problems, such that expression of one or more genes may be affected.

Expression of heterologous DNA sequences in a plant host is dependent upon the presence of an operably linked promoter that is functional within the plant host. Choice of the promoter sequence will determine when and where within the organism the heterologous DNA sequence is expressed. Thus, where expression is desired in a preferred tissue of a plant, tissue-preferred promoters are utilized. In contrast, where gene expression throughout the cells of a plant is desired, constitutive promoters are the regulatory element of choice. Additional regulatory sequences upstream and/or downstream from the core promoter sequence may be included in expression constructs of transformation vectors to bring about varying levels of tissue-preferred or constitutive expression of heterologous nucleotide sequences in a transgenic plant.

Isolation and characterization of root-preferred promoters and terminators that can serve as regulatory elements for expression of isolated nucleotide sequences of interest in a root-preferred manner are needed for impacting various traits in plants and in use with scorable markers. The inventors have isolated just such a promoter and terminator.

SUMMARY OF THE INVENTION

The invention is to a regulatory element that regulates transcription in a root-preferred manner.

In an embodiment, the regulatory element drives transcription in a root-preferred manner, wherein said regulatory element comprises a nucleotide sequence selected from the group consisting of: a) sequences natively associated with, and that regulate expression of DNA coding for maize 6-phosphogluconate dehydrogenase (6PGD); b) the nucleotide sequence set forth in either of SEQ ID NO: 2; or c) a sequence comprising a fragment of the nucleotide sequence set forth in either of SEQ ID NO: 2 or 4. In another embodiment of the invention the regulatory element comprises SEQ ID NO: 10 ("1st truncation"). In a further embodiment, the regulatory element comprises SEQ ID NO: 11 ("2nd truncation").

Further embodiments are to expression cassettes, transformation vectors, plants, plant cells and plant parts comprising the above nucleotide sequences. The invention is further to methods of using the sequence in plants and plant cells. An embodiment of the invention further comprises the nucleotide sequences described above comprising a detectable marker.

DETAILED DESCRIPTION OF THE INVENTION

Figure 1:
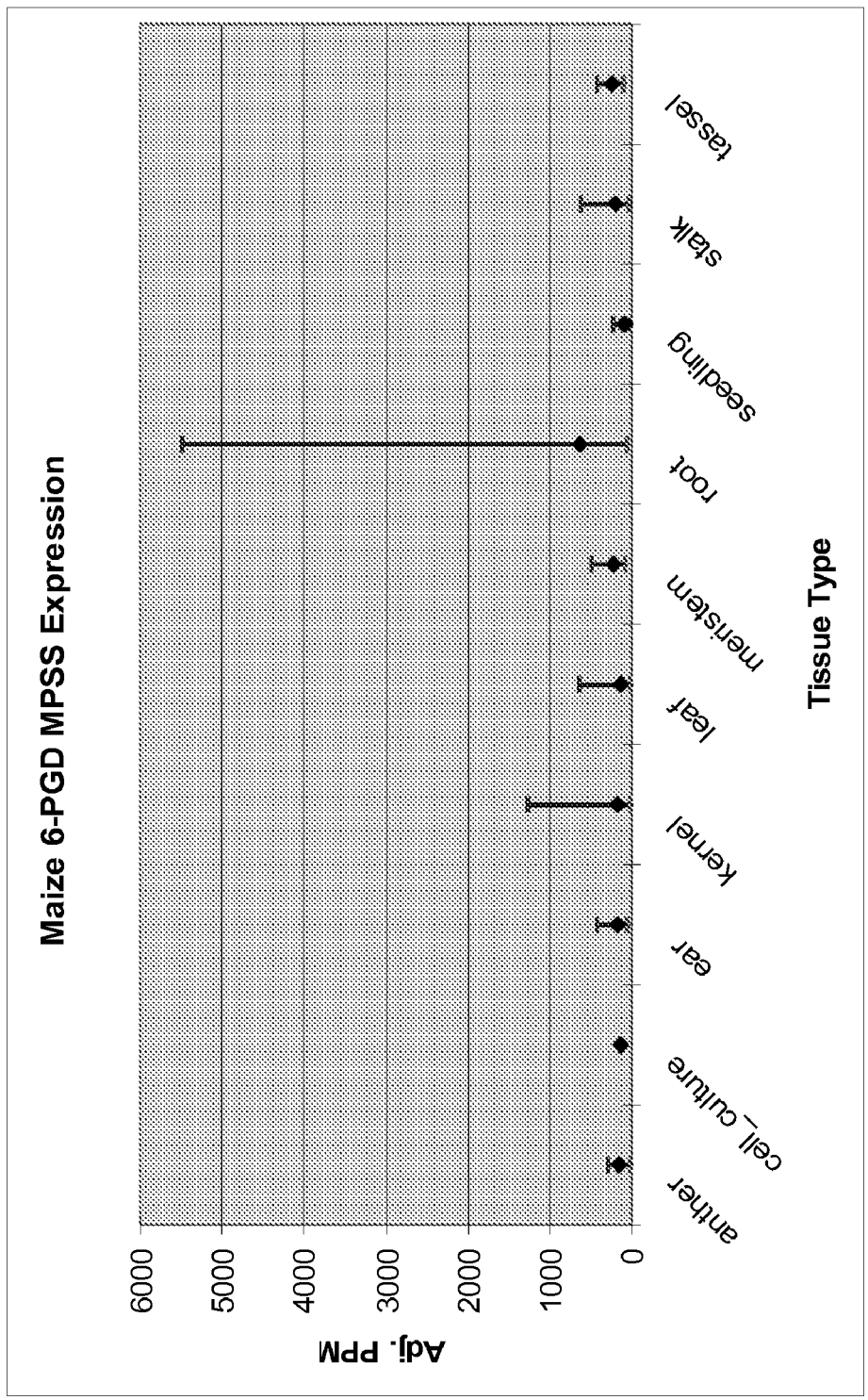
FIG. 1. Average expression levels of maize 6-PGD gene in MPSS libraries from different tissues, shown with maximum PPM (top), mean PPM (dot) and minimum PPM (bottom). The peak expression is in a root library at 5486 PPM, and the lowest level of expression was 2 PPM found in another and kernel. Note the root and kernel tissue have the highest overall expression.

In accordance with the invention, nucleotide sequences are provided that allow regulation of transcription in root. The sequences of the invention comprise regulatory elements associated with root formation and root tissues. Thus, the compositions of the present invention comprise novel nucleotide sequences for plant regulatory elements natively associated with the nucleotide sequences coding for 6PGD.

The enzyme 6-Phosphogluconate Dehydrogenase (6-PGD) catalyze a key step in the oxidative pentose phosphate pathway by decarboxylating 6-phosphogluconate to ribulose-5-P and $CO_2$ and generates a molecule of NADPH. The enzyme was shown to have high activities in maize roots (Bailey-Serres and Nguyen (1992) *Plant Physiol.* 100: 1580-

1583), with tissue- and cell type-specific expression (Bailey-Serres, et al., (1992) *Biochem Genet.* 30: 233-46). The enzyme activity was also high in mature scutella (Bailey-Serres and Nguyen (1992)). The 6GPD promoter enhances production of this important enzyme.

Such a promoter is also useful to target sequences encoding proteins for disease resistance to the root. Additionally, linking a promoter which preferentially expresses to the root with a marker, and, in particular, a visual marker, is useful in tracking the expression of a linked gene of interest.

A method for expressing an isolated nucleotide sequence in a plant using the regulatory sequences disclosed herein is provided. The method comprises transforming a plant cell with a transformation vector that comprises an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in a root-preferred manner.

Frequently it is desirable to have preferential expression of a DNA sequence in a tissue of an organism. For example, increased resistance of a plant to insect attack might be accomplished by genetic manipulation of the plant's genome to comprise a tissue-specific promoter operably linked to a heterologous insecticide gene such that the insect-deterring substances are specifically expressed in the susceptible plant tissues. Preferential expression of the heterologous nucleotide sequence in the appropriate tissue reduces the drain on the plant's resources that occurs when a constitutive promoter initiates transcription of a heterologous nucleotide sequence throughout the cells of the plant.

Alternatively, it might be desirable to inhibit expression of a native DNA sequence within a plant's tissues to achieve a desired phenotype. In this case, such inhibition might be accomplished with transformation of the plant to comprise a tissue-specific promoter operably linked to an antisense nucleotide sequence, such that tissue-specific expression of the antisense sequence produces an RNA transcript that interferes with translation of the mRNA of the native DNA sequence in a subset of the plant's cells.

Under the regulation of the root-specific regulatory elements will be a sequence of interest, which will provide for modification of the phenotype of the root. Such modification includes modulating the production of an endogenous product, as to amount, relative distribution, or the like, or production of an exogenous expression product to provide for a novel function or product in the root.

Definitions

By "root-preferred" is intended favored expression in the plant root, the root vasculature of a plant, and the like.

By "regulatory element" is intended sequences responsible expression of the associated coding sequence including, but not limited to, promoters, terminators, enhancers, introns, and the like.

By "terminator" is intended sequences that are needed for termination of transcription: a regulatory region of DNA that causes RNA polymerase to disassociate from DNA, causing termination of transcription.

By "promoter" is intended a regulatory region of DNA capable of regulating the transcription of a sequence linked thereto. It usually comprises a TATA box capable of directing RNA polymerase II to initiate RNA synthesis at the appropriate transcription initiation site for a particular coding sequence.

A promoter may additionally comprise other recognition sequences generally positioned upstream or 5' to the TATA box, referred to as upstream promoter elements, which influence the transcription initiation rate and further include elements which impact spatial and temporal expression of the linked nucleotide sequence. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein may comprise upstream regulatory elements such as those responsible for tissue and temporal expression of the coding sequence, and may include enhancers, the DNA response element for a transcriptional regulatory protein, ribosomoal binding sites, transcriptional start and stop sequences, translational start and stop sequences, activator sequence and the like.

In the same manner, the promoter elements which enable expression in the desired tissue such as the root can be identified, isolated, and used with other core promoters to confirm root-preferred expression. By core promoter is meant the minimal sequence required to initiate transcription, such as the sequence called the TATA box which is common to promoters in genes encoding proteins. Thus the upstream promoter of 6PGD can optionally be used in conjunction with its own or core promoters from other sources. The promoter may be native or non-native to the cell in which it is found.

The isolated promoter sequence of the present invention can be modified to provide for a range of expression levels of the isolated nucleotide sequence. Less than the entire promoter region can be utilized and the ability to drive root-preferred expression retained. It is recognized that expression levels of mRNA can be modulated with specific deletions of portions of the promoter sequence. Thus, the promoter can be modified to be a weak or strong promoter. Generally, by "weak promoter" is intended a promoter that drives expression of a coding sequence at a low level. By "low level" is intended levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region or 5' untranslated region (5' UTR). Likewise the terminator can be isolated from the 3' region flanking its respective stop codon. The term "isolated" refers to material, such as a nucleic acid or protein, which is: (1) substantially or essentially free from components which normally accompany or interact with the material as found in its naturally occurring environment; or (2) if the material is in its natural environment, the material has been altered by deliberate human intervention to a composition and/or placed at a locus in a cell other than the locus native to the material. Methods for isolation of promoter regions are well known in the art.

The complete genomic sequences for maize 6PGD gene set forth in SEQ ID NO: 1 is 2655 nucleotides in length. The maize 6PGD promoter is set forth in SEQ ID NO: 2, 889 nucleotides in length, isolated from the *Zea mays* 6PGD coding region with the 5'-UTR double-underlined. The 6PGD transcript is shown in SEQ ID NO: 3, and the terminator region is shown in italics and underlined (SEQ ID NO: 4). It was isolated based on MPSS (Massively Parallel Signature Sequencing) technology from LYNX™ (see, Brenner, et al., (2000) *Nature Biotechnology* 18: 630-634) expression analysis showing strong expression in V4-5 stage maize roots. The 6PGD promoter can address expression problems by providing this pattern of expression.

Figure 2:
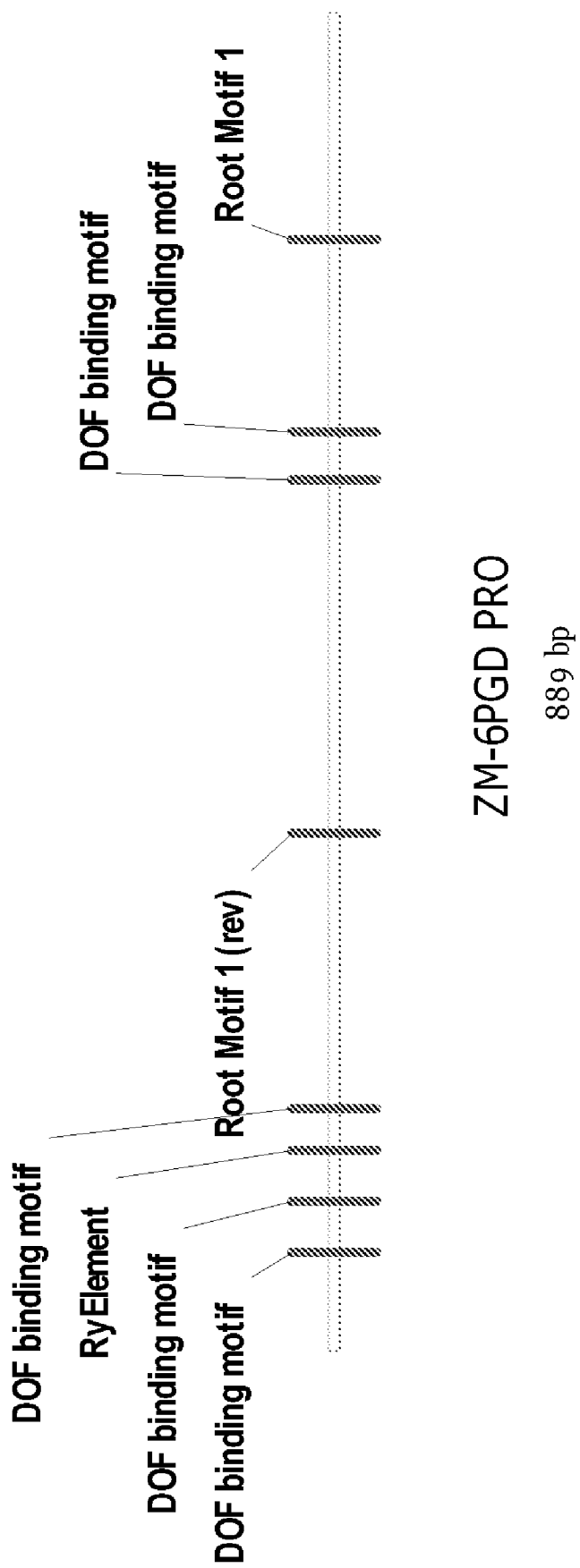
FIG. 2. Vector NTI map depicting the 6PGD promoter and motif locations (DOF binding motif at positions 65-68, 99-102, 161-164, 579-582 and 611-614, Ry Element at 133-139, and Root Motif 1—forward at 739-743 and reverse direction at 348-344).

Motifs of about 4-7 bases within the 6PGD promoter sequence were discovered by searching for sequences of similar size and within 100 bases of the position in which they were located. The following motifs are found in the 6PGD promoter as represented in Table 1, and FIG. 2.

TABLE 1

| Name | Sequence | Location | Function | Reference |
|---|---|---|---|---|
| Root Motif 1 | ATATT | 739-743; 348-344 (rev) | Root expression | Elmayan and Tepfer 1995 Transgenic Res 4: 388-396 |
| Ry Element | CATGCAA | 133-139 | Seed development | Bobb et al 1997 Nucleic Acids Res. 25: 641-647 |
| DOF binding motif | AAAG | 65-68; 99-102; 161-164; 579-582; 611-614 | DNA binding | Yanagisawa 2002 Trends Plant Sci. 7: 555-560. |

The promoter regions of the invention may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers. Preferably, plants include corn, soybean, sunflower, safflower, canola, wheat, barley, rye, alfalfa, and sorghum.

Promoter sequences from other plants may be isolated according to well-known techniques based on their sequence homology to the homologous coding region of the coding sequences set forth herein. In these techniques, all or part of the known coding sequence is used as a probe which selectively hybridizes to other sequences present in a population of cloned genomic DNA fragments (i.e., genomic libraries) from a chosen organism. Methods are readily available in the art for the hybridization of nucleic acid sequences. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

"Functional variants" of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

As used herein, a "functional fragment" is a regulatory sequence variant formed by one or more deletions from a larger regulatory element. For example, the 5' portion of a promoter up to the TATA box near the transcription start site can be deleted without abolishing promoter activity, as described by Opsahl-Sorteberg, H-G., et al., (2004) "Identification of a 49-bp fragment of the HvLTP2 promoter directing aleruone cell specific expression" *Gene* 341: 49-58. Such variants should retain promoter activity, particularly the ability to drive expression in root or root tissues. Activity can be measured by Northern blot analysis, reporter activity measurements when using transcriptional fusions, and the like. See, for example, Sambrook, et al., (1989) *Molecular Cloning: A Laboratory Manual* (2nd ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis, et al., (1987) *Methods Enzymol.* 155: 335-350, and Erlich, ed. (1989) *PCR Technology* (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g., Innis, et al., (1990) *PCR Protocols, A Guide to Methods and Applications*, eds., Academic Press). Primers used for isolation of the root-preferred promoter sequences are listed as SEQ ID NOS: 5-9.

The root-preferred regulatory elements disclosed in the present invention, as well as variants and fragments thereof, are useful in the genetic manipulation of any plant when operably linked with an isolated nucleotide sequence of interest whose expression is to be controlled to achieve a desired phenotypic response.

By "operably linked" is intended a functional linkage between a promoter and a second sequence, wherein the promoter sequence initiates and mediates transcription of the DNA sequence corresponding to the second sequence. The expression cassette will include 5' and 3' regulatory sequences operably linked to at least one of the sequences of the invention.

In one typical embodiment, in the context of an over expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The regulatory elements of the invention can be operably linked to the isolated nucleotide sequence of interest in any of several ways known to one of skill in the art. The isolated nucleotide sequence of interest can be inserted into a site within the genome which is 3' to the promoter of the invention using site specific integration as described in U.S. Pat. No. 6,187,994 herein incorporated in it's entirety by reference.

The regulatory elements of the invention can be operably linked in expression cassettes along with isolated nucleotide sequences of interest for expression in the desired plant, more particularly in the root of the plant. Such an expression cassette is provided with a plurality of restriction sites for insertion of the nucleotide sequence of interest under the transcriptional control of the regulatory elements.

The isolated nucleotides of interest expressed by the regulatory elements of the invention can be used for directing expression of a sequence in plant tissues. This can be achieved by increasing expression of endogenous or exogenous products in root. Alternatively, the results can be achieved by providing for a reduction of expression of one or more endogenous products, particularly enzymes or cofactors in the root. This down regulation can be achieved through many different approaches known to one skilled in the art, including antisense, cosuppression, use of hairpin formations, or others, and discussed infra. Importation or exportation of a cofactor also allows for control of root composition. It is recognized that the regulatory elements may be used with their native or other coding sequences to increase or decrease expression of an operably linked sequence in the transformed plant or seed.

General categories of genes of interest for the purposes of the present invention include for example, those genes involved in information, such as zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms.

Modifications that affect grain traits include increasing the content of oleic acid, or altering levels of saturated and unsaturated fatty acids. Likewise, the level of root proteins, particularly modified root proteins that improve the nutrient value of the root, can be increased. This is achieved by the expression of such proteins having enhanced amino acid content.

Increasing the levels of lysine and sulfur-containing amino acids may be desired as well as the modification of starch type and content in the seed. Hordothionin protein modifications are described in WO 9416078 filed Apr. 10, 1997; WO 9638562 filed Mar. 26, 1997; WO 9638563 filed Mar. 26, 1997 and U.S. Pat. No. 5,703,409 issued Dec. 30, 1997. Another example is lysine and/or sulfur-rich root protein encoded by the soybean 2S albumin described in WO 9735023 filed Mar. 20, 1996, and the chymotrypsin inhibitor from barley, Williamson, et al., (1987) *Eur. J. Biochem.* 165: 99-106.

Agronomic traits in roots can be improved by altering expression of genes that: affect the response of root, plant or seed growth and development during environmental stress, Cheikh-N, et al., (1994) *Plant Physiol.* 106(1): 45-51 and genes controlling carbohydrate metabolism to reduce kernel abortion in maize, Zinselmeier, et al., (1995) *Plant Physiol.* 107(2): 385-391.

It is recognized that any gene of interest, including the native coding sequence, can be operably linked to the regulatory elements of the invention and expressed in the root.

By way of illustration, without intending to be limiting, are examples of the types of genes which can be used in connection with the regulatory sequences of the invention.

1. Transgenes that confer resistance to Insects or disease and that encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266: 789 (cloning of the tomato Cf-9 gene for resistance to *Cladosporium fulvum*); Martin, et al., (1993) Science 262: 1432 (tomato Pto gene for resistance to *Pseudomonas syringae* pv. tomato encodes a protein kinase); Mindrinos, et al., (1994) *Cell* 78: 1089 (Arabidopsis RSP2 gene for resistance to *Pseudomonas syringae*); McDowell and Woffenden, (2003) *Trends Biotechnol.* 21(4): 178-83 and Toyoda, et al., (2002) *Transgenic Res.* 11(6): 567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser, et al., (1986) *Gene* 48: 109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Numbers 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; PCT Application Numbers WO 91/14778; WO 99/31248; WO 01/12731; WO 99/24581; WO 97/40162 and U.S. application Ser. Nos. 10/032,717; 10/414,637; and 10/606,320.

(C) An insect-specific hormone or pheromone such as an ecdysteroid and juvenile hormone, a variant thereof, a mimetic based thereon, or an antagonist or agonist thereof. See, for example, the disclosure by Hammock, et al., (1990) *Nature* 344: 458, of baculovirus expression of cloned juvenile hormone esterase, an inactivator of juvenile hormone.

(D) An insect-specific peptide which, upon expression, disrupts the physiology of the affected pest. For example, see the disclosures of Regan, (1994) *J. Biol. Chem.* 269: 9 (expression cloning yields DNA coding for insect diuretic hormone receptor); Pratt, et al., (1989) *Biochem. Biophys. Res. Comm.* 163: 1243 (an allostatin is identified in *Diploptera puntata*); Chattopadhyay, et al., (2004) *Critical Reviews in Microbiology* 30(1): 33-54; Zjawiony, (2004) *J Nat Prod* 67(2): 300-310; Carlini and Grossi-de-Sa, (2002) *Toxicon* 40(11): 1515-1539; Ussuf, et al., (2001) *Curr Sci.* 80(7): 847-853; and Vasconcelos and Oliveira (2004) *Toxicon* 44(4): 385-403. See also, U.S. Pat. No. 5,266,317 to Tomalski, et al., who disclose genes encoding insect-specific toxins.

(E) An enzyme responsible for a hyperaccumulation of a monoterpene, a sesquiterpene, a steroid, hydroxycinnamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application Number WO 93/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) *Insect Biochem. Molec. Biol.* 23: 691, who teach the nucleotide sequence of a cDNA encoding tobacco hookworm chitinase; and Kawalleck, et al., (1993) *Plant Molec. Biol.* 21: 673, who provide the nucleotide sequence of the parsley ubi4-2 polyubiquitin gene; U.S. application Ser. Nos. 10/389,432, 10/692,367, and U.S. Pat. No. 6,563,020.

(G) A molecule that stimulates signal transduction. For example, see the disclosure by Botella, et al., (1994) *Plant Molec. Biol.* 24: 757, of nucleotide sequences for mung bean calmodulin cDNA clones; and Griess, et al., (1994) *Plant Physiol.* 104: 1467, who provide the nucleotide sequence of a maize calmodulin cDNA clone.

(H) A hydrophobic moment peptide. See, PCT Application Number WO 95/16776 and U.S. Pat. No. 5,580,852 (disclosure of peptide derivatives of Tachyplesin which inhibit fungal plant pathogens) and PCT Application Number WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes, et al., (1993) *Plant Sci.* 89: 43, of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28: 451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf., Taylor, et al., Abstract #497, *Seventh Int'l Symposium on Molecular Plant-microbe Interactions* (Edinburgh, Scotland, 1994) (enzymatic inactivation in transgenic tobacco via production of single-chain antibody fragments).

(L) A virus-specific antibody. See, for example, Tavladoraki, et al. (1993), *Nature* 366: 469, who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10: 1436. The cloning and characterization of a gene which encodes a bean endopolygalacturonase-inhibiting protein is described by Toubart, et al., (1992) *Plant J.* 2: 367.

(N) A developmental-arrestive protein produced in nature by a plant. For example, Logemann, et al., (1992) *Bio/Technology* 10: 305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology,* 5(2): 128-131; Pieterse and Van Loon (2004) *Curr. Opin. Plant Bio.* 7(4): 456-64 and Somssich, (2003) *Cell* 113(7): 815-6.

(P) Antifungal genes (Cornelissen and Melchers, (1993) *Pl. Physiol.* 101: 709-712; Parijs, et al., (1991) *Planta* 183: 258-264; and Bushnell, et al., (1998) *Can. J. of Plant Path.* 20(2): 137-149. Also see, U.S. application Ser. No. 09/950, 933.

(Q) Detoxification genes, such as for fumonisin, beauvericin, moniliformin and zearalenone and their structurally related derivatives. For example, see U.S. Pat. No. 5,792,931.

(R) Cystatin and cysteine proteinase inhibitors. See, U.S. application Ser. No. 10/947,979.

(S) Defensin genes. See, PCT Application Number WO 03/000863 and U.S. application Ser. No. 10/178,213.

(T) Genes conferring resistance to nematodes. See, PCT Application Number WO 03/033651 and Urwin, et. al., (1998) *Planta* 204: 472-479; Williamson (1999) *Curr Opin Plant Bio.* 2(4): 327-31.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035.

2. Transgenes that confer resistance to a herbicide such as:

(A) An herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7: 1241; and Miki, et al., (1990) *Theor. Appl. Genet.* 80: 449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; and PCT Application Number WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; Re. 36,449; RE 37,287 E; and 5,491,288; and international publication numbers EP1173580; WO 01/66704; EP1173581 and EP1173582. Glyphosate resistance is also imparted to plants that express a gene that encodes a glyphosate oxido-reductase enzyme as described more fully in U.S. Pat. Nos. 5,776,760 and 5,463,175. In addition glyphosate resistance can be imparted to plants by the over expression of genes encoding glyphosate N-acetyltransferase. See, for example, U.S. application Ser. Nos. 01/46227; 10/427,692 and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in European Patent Number 0 242 246 and 0 242 236 to Leemans, et al. De Greef, et al., (1989) *Bio/Technology* 7: 61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616; and 5,879,903. Exemplary genes conferring resistance to phenoxy proprionic acids and cycloshexones, such as sethoxydim and haloxyfop, are the Acc1-S1, Acc1-S2 and Acc1-S3 genes described by Marshall, et al., (1992) *Theor. Appl. Genet.* 83: 435.

(C) A herbicide that inhibits photosynthesis, such as a triazine (psbA and gs+ genes) and a benzonitrile (nitrilase gene). Przibilla, et al., (1991) *Plant Cell* 3: 169, describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Numbers 53435, 67441 and 67442. Cloning and expression of DNA coding for a glutathione S-transferase is described by Hayes, et al., (1992) *Biochem. J.* 285: 173.

(D) Acetohydroxy acid synthase, which has been found to make plants that express this enzyme resistant to multiple types of herbicides, has been introduced into a variety of plants (see, e.g., Hattori, et al., (1995) *Mol Gen Genet.* 246: 419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol.* 106: 17), genes for glutathione reductase and superoxide dismutase (Aono, et al., (1995) *Plant Cell Physiol* 36: 1687, and genes for various phosphotransferases (Datta, et al., (1992) *Plant Mol Biol* 20: 619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; and 5,767,373; and international publication WO 01/12825.

3. Transgenes That Confer Or Contribute To an Altered Grain Characteristic, Such As:

(A) Altered fatty acids, for example, by
 (1) Down-regulation of stearoyl-ACP desaturase to increase stearic acid content of the plant. See, Knultzon, et al., (1992) *Proc. Natl. Acad. Sci. USA* 89: 2624 and PCT Application Number WO 99/64579 (Genes for Desaturases to Alter Lipid Profiles in Corn),
 (2) Elevating oleic acid via FAD-2 gene modification and/or decreasing linolenic acid via FAD-3 gene modification (see, U.S. Pat. Nos. 6,063,947; 6,323,392; 6,372,965 and PCT Application Number WO 93/11245),
 (3) Altering conjugated linolenic or linoleic acid content, such as in PCT application Number WO 01/12800,
 (4) Altering LEC1, AGP, Dek1, Superal1, milps, various Ipa genes such as Ipa1, Ipa3, hpt or hggt. For example, see, PCT Application Numbers WO 02/42424, WO 98/22604, WO 03/011015, U.S. Pat. Nos. 6,423,886, 6,197,561, 6,825,397, US Application Publication Number 2003/0079247, US Application Publication Number 2003/0204870, PCT Application Numbers WO 02/057439, WO 03/011015 and Rivera-Madrid, et. al., (1995) *Proc. Natl. Acad. Sci.* 92: 5620-5624.

(B) Altered phosphorus content, for example, by the
 (1) Introduction of a phytase-encoding gene would enhance breakdown of phytate, adding more free phosphate to the transformed plant. For example, see, Van Hartingsveldt, et al., (1993) *Gene* 127: 87, for a disclosure of the nucleotide sequence of an *Aspergillus niger* phytase gene.
 (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35: 383 and/or by altering inositol kinase activity as in PCT Application Number WO 02/059324, US Application Publication Number 2003/0009011, PCT Application Number WO 03/027243, US Application Publication Number 2003/0079247, PCT Application Number WO 99/05298, U.S. Pat. Nos. 6,197,561, 6,291,224, 6,391,348, PCT Application Number WO 2002/059324, US Application Publication Number 2003/0079247, PCT Application Numbers WO 98/45448, WO 99/55882, WO 01/04147.

(C) Altered carbohydrates effected, for example, by altering a gene for an enzyme that affects the branching pattern of starch or a gene altering thioredoxin. (See, U.S. Pat. No. 6,531,648). See, Shiroza, et al., (1988) *J. Bacteriol.* 170: 810 (nucleotide sequence of *Streptococcus mutans* fructosyltransferase gene); Steinmetz, et al., (1985) *Mol. Gen. Genet.* 200: 220 (nucleotide sequence of *Bacillus subtilis* levansucrase gene); Pen, et al., (1992) *Bio/Technology* 10: 292 (production of transgenic plants that express *Bacillus licheniformis* alpha-amylase); Elliot, et al., (1993) *Plant Molec. Biol.* 21 515 (nucleotide sequences of tomato invertase genes); Søgaard, et al., (1993) *J. Biol. Chem.* 268: 22480 (site-directed mutagenesis of barley alpha-amylase gene); and Fisher, et al., (1993) *Plant Physiol.* 102: 1045 (maize endosperm starch branching enzyme II), WO Application Number 99/10498 (improved digestibility and/or starch extraction through modification of UDP-D-xylose 4-epimerase, Fragile 1 and 2, Ref1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Application Serial Number 2004/0034886 and PCT Application Number WO 00/68393 involving the manipulation of antioxidant levels through alteration of a phytl prenyl transferase (ppt), WO Application Number 03/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), Application Number WO 99/40209 (alteration of amino acid compositions in seeds), PCT Application Number WO 99/29882 (methods for altering amino acid content of proteins), U.S. Pat. No. 5,850,016 (alteration of amino acid compositions in seeds), PCT Application Number WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), PCT Application Number WO 98/56935 (plant amino acid biosynthetic enzymes), PCT Application Number WO 98/45458 (engineered seed protein having higher percentage of essential amino acids), PCT Application Number WO 98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), PCT Application Number WO 96/01905 (increased threonine), PCT Application Number WO 95/15392 (increased lysine), US Application Publication Number 2003/0163838, US Application Publication Number 2003/0150014, US Application Publication Number 2004/0068767, U.S. Pat. No. 6,803,498, PCT Application Number WO 01/79516, and PCT Application Number WO 00/09706 (Ces A: cellulose synthase), U.S. Pat. No. 6,194,638 (hemicellulose), U.S. Pat. No. 6,399,859 and US Application Publication Number 2004/0025203 (UDPGdH), U.S. Pat. No. 6,194,638 (RGP).

4. Genes that Control Male-sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (PCT Application Number WO 01/29237).

(B) Introduction of various stamen-specific promoters (PCT Application Numbers WO 92/13956, WO 92/13957).

(C) Introduction of the barnase and the barstar gene (Paul, et al., (1992) *Plant Mol. Biol.* 19: 611-622).

For additional examples of nuclear male and female sterility systems and genes, see also, U.S. Pat. Nos. 5,859,341; 6,297,426; 5,478,369; 5,824,524; 5,850,014 and 6,265,640.

5. Genes that create a site for site specific DNA integration.

This includes the introduction of FRT sites that may be used in the FLP/FRT system and/or Lox sites that may be used in the Cre/Loxp system. For example, see, Lyznik, et al., (2003) "Site-Specific Recombination for Genetic Engineering in Plants" *Plant Cell Rep* 21: 925-932 and PCT Application Number WO 99/25821, which are hereby incorporated by reference. Other systems that may be used include the Gin recombinase of phage Mu (Maeser, et al., (1991) *Mol Gen Genet.* 230(1-2): 170-6); Vicki Chandler, The Maize Handbook ch. 118 (Springer-Verlag 1994), the Pin recombinase of *E. coli* (Enomoto, et al., 1983) and the R/RS system of the pSR1 plasmid (Araki, et al., (1992) *J Mol. Biol.* 225(1):25-37.

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress.

For example, see, PCT Application Number WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, PCT Application Numbers WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; US Publication Number 2004/0148654 and PCT Application Number WO 01/36596 where abscisic acid is altered in plants resulting in improved plant phenotype such as increased yield and/or increased tolerance to abiotic stress; PCT Application Numbers WO 2000/006341, WO 04/090143, U.S. application Ser. Nos. 10/817,483 and 09/545,334 where cytokinin expression is modified resulting in plants with increased stress tolerance, such as drought tolerance, and/or increased yield. Also see, PCT Application Numbers WO 02/02776, WO 2003/052063, JP 2002281975, U.S. Pat. No. 6,084,153, PCT Application Number WO 0164898, U.S. Pat. Nos. 6,177,275, and 6,107, 547 (enhancement of nitrogen utilization and altered nitrogen responsiveness). For ethylene alteration, see, US Application Publication Number 20040128719, US Application Publication Number 20030166197 and PCT Application Number WO 2000/32761. For plant transcription factors or transcriptional regulators of abiotic stress, see, e.g., US Application Publication Number 20040098764 or US Application Publication Number 20040078852.

Other genes and transcription factors that affect plant growth and agronomic traits such as yield, flowering, plant growth and/or plant structure, nutrient uptake, especially nitrogen uptake by plants, nitrogen use efficiency; drought tolerance and water use efficiency; root strength, and root lodging resistance; soil pest management, corn root worm resistance can be introduced or introgressed into plants, see e.g., PCT Application Numbers WO 97/49811 (LHY), WO 98/56918 (ESD4), WO 97/10339 and U.S. Pat. No. 6,573,430 (TFL), U.S. Pat. No. 6,713,663 (FT), PCT Application Numbers WO 96/14414 (CON), WO 96/38560, WO 01/21822 (VRN1), WO 00/44918 (VRN2), WO 99/49064 (GI), WO 00/46358 (FR1), WO 97/29123, U.S. Pat. Nos. 6,794,560, 6,307,126 (GAI), PCT Application Numbers WO 99/09174 (D8 and Rht), and WO 2004/076638 and WO 2004/031349 (transcription factors).

Commercial traits in plants can be created through the expression of genes that alter starch or protein for the production of paper, textiles, ethanol, polymers or other materials with industrial uses.

Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering (see, Nobrega, et. al., (2004) *Nature* 431: 988-993), homologous recombination, TILLING (Targeting Induced Local Lesions In Genomes), and biosynthetic competition to manipulate, the expression of proteins.

Many techniques for gene silencing are well known to one of skill in the art, including but not limited to knock-outs such as by insertion of a transposable element such as Mu, Vicki Chandler, *The Maize Handbook* ch. 118 (Springer-Verlag 1994) or other genetic elements such as a FRT, Lox or other site specific integration site; RNA interference (Napoli, et al., (1990) *Plant Cell* 2: 279-289; U.S. Pat. No. 5,034,323, Sharp (1999) *Genes Dev.* 13: 139-141, Zamore, et al., (2000) *Cell* 101: 25-33; and Montgomery, et al., (1998) *PNAS USA* 95:15502-15507); virus-induced gene silencing (Burton, et al., (2000) *Plant Cell* 12: 691-705, and Baulcombe (1999) *Curr. Op. Plant Bio.* 2:109-113); target-RNA-specific ribozymes (Haseloff, et al., (1988) *Nature* 334: 585-591); hairpin structures (Smith, et al., (2000) *Nature* 407: 319-320; PCT Application Numbers WO 99/53050; and WO 98/53083); MicroRNA (Aukerman and Sakai (2003) *Plant Cell* 15: 2730-2741); ribozymes (Steinecke, et al., (1992) *EMBO J.* 11: 1525, and Perriman, et al., (1993) *Antisense Res. Dev.* 3: 253); oligonucleotide mediated targeted modification (e.g., PCT Application Numbers WO 03/076574 and WO 99/25853); zinc-finger targeted molecules (e.g., PCT Application Numbers WO 01/52620; WO 03/048345; and WO 00/42219); and other methods or combinations of the above methods known to those of skill in the art.

Any method of increasing or inhibiting a protein can be used in the present invention. Several examples are outlined in more detail below for illustrative purposes.

The nucleotide sequence operably linked to the regulatory elements disclosed herein can be an antisense sequence for a targeted gene. (See, e.g., Sheehy, et al., (1988) *PNAS USA* 85: 8805-8809; and U.S. Pat. Nos. 5,107,065; 5,453,566 and 5,759,829). By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant root.

As noted, other potential approaches to impact expression of proteins in the root include traditional co-supression, that is, inhibition of expression of an endogenous gene through the expression of an identical structural gene or gene fragment introduced through transformation (Goring, et al., (1991) *Proc. Natl. Acad. Sci. USA* 88: 1770-1774 co-suppression; Taylor (1997) *Plant Cell* 9: 1245; Jorgensen (1990) *Trends Biotech.* 8(12): 340-344; Flavell (1994) *PNAS USA* 91: 3490-3496; Finnegan, et al., (1994) *Bio/Technology* 12: 883-888; and Neuhuber, et al., (1994) *Mol. Gen. Genet.* 244: 230-241). In one example, co-supression can be achieved by linking the promoter to a DNA segment such that transcripts of the segment are produced in the sense orientation and where the transcripts have at least 65% sequence identity to transcripts of the endogenous gene of interest, thereby supressing expression of the endogenous gene in said plant cell. (See, U.S. Pat. No. 5,283,184). The endogenous gene targeted for co-suppression may be a gene encoding any protein that accumulates in the plant species of interest. For example, where the endogenous gene targeted for co-suppression is the 50 kD gamma-zein gene, co-suppression is achieved using an expression cassette comprising the 50 kD gamma-zein gene sequence, or variant or fragment thereof.

Additional methods of co-suppression are known in the art and can be similarly applied to the instant invention. These methods involve the silencing of a targeted gene by spliced hairpin RNA's and similar methods also called RNA interference and promoter silencing (see, Smith, et al., (2000) *Nature* 407: 319-320, Waterhouse and Helliwell (2003) *Nat. Rev. Genet.* 4: 29-38; Waterhouse, et al., (1998) *Proc. Natl. Acad. Sci. USA* 95: 13959-13964; Chuang and Meyerowitz (2000) *Proc. Natl. Acad. Sci. USA* 97: 4985-4990; Stoutjesdijk, et al., (2002) *Plant Phystiol.* 129: 1723-1731; and PCT Application Numbers WO 99/53050; WO 99/49029; WO 99/61631; WO 00/49035 and U.S. Pat. No. 6,506,559.)

For mRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants.

In one embodiment, the polynucleotide to be introduced into the plant comprises an inhibitory sequence that encodes a zinc finger protein that binds to a gene encoding a protein of the invention resulting in reduced expression of the gene. In particular embodiments, the zinc finger protein binds to a regulatory region of a gene of the invention. In other embodiments, the zinc finger protein binds to a messenger RNA encoding a protein and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Publication Number 2003/0037355.

The expression cassette may also include at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source.

The 6PGD terminator set forth in SEQ ID NO: 4 is 269 nucleotides in length. The coding region was identified according to the procedure described in Woo, et al., (2001) *Journal Plant Cell* 13(10): 2297-2317 incorporated herein by reference. The 6PGD terminator can be used with the 6PGD promoter in an expression cassette, or can be used with another appropriate promoter to provide root-preferred expression of a coding region.

Any convenient termination regions can be used in conjunction with the promoter of the invention, and are available from the Ti-plasmid of *A. tumefaciens*, such as the octopine synthase and nopaline synthase termination regions. See also, Guerineau, et al., (1991) *Mol. Gen. Genet.* 262: 141-144; Proudfoot (1991) *Cell* 64: 671-674; Sanfacon, et al., (1991) *Genes Dev.* 5: 141-149; Mogen, et al., (1990) *Plant Cell* 2: 1261-1272; Munroe, et al., (1990) *Gene* 91: 151-158; Ballas, et al., (1989) *Nucleic Acids Res.* 17: 7891-7903; Joshi, et al., (1987) *Nucleic Acid Res.* 15: 9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein, et al., (1989) *Proc. Natl. Acad. Sci. USA* 86: 6126-6130; potyvirus leaders, for example, TEV leader (Tobacco Etch Virus), Allison, et al., (1986) "The Nucleotide Sequence of the Coding Region of Tobacco Etch Virus Genomic RNA: Evidence for the Synthesis of a Single Polyprotein", *Virology* 154: 9-20; MDMV leader (Maize Dwarf Mosaic Virus); human immunoglobulin heavy-chain binding protein (BiP), Macejak, et al., (1991) *Nature* 353: 90-94; untranslated leader from the coat protein mRNA of alfalfa mosaic virus (AMV RNA 4), Jobling, et al., (1987) *Nature* 325: 622-625); tobacco mosaic virus leader (TMV), Gallie, et al., (1989) *Molecular Biology of RNA, pages* 237-256; and maize chlorotic mottle virus leader (MCMV), Lommel, et al., (1991) *Virology* 81: 382-385. See also, Della-Cioppa, et al., (1987) *Plant Physiology* 84: 965-968. The cassette can also contain sequences that enhance translation and/or mRNA stability such as introns.

In those instances where it is desirable to have an expressed product of an isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook, et al. (supra).

The transformation vector comprising the regulatory sequences of the present invention operably linked to an isolated nucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene to be expressed under control of the regulatory elements of the present invention. In one embodiment, a selectable marker and a reporter gene are also included. For ease of obtaining sufficient quantities of vector, a bacterial origin that allows replication in *E. Coli* can be used.

Reporter genes can be included in the transformation vectors. Examples of suitable reporter genes known in the art can be found in, for example, Jefferson, et al., (1991) in *Plant Molecular Biology Manual*, ed. Gelvin, et al., (Kluwer Academic Publishers), pp. 1-33; DeWet, et al., (1987) *Mol. Cell. Biol.* 7: 725-737; Goff, et al., (1990) *EMBO J.* 9: 2517-2522; Kain, et al., (1995) *BioTechniques* 19: 650-655; and Chiu, et al., (1996) *Current Biology* 6: 325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella, et al., (1983) *EMBO J.* 2: 987-992; methotrexate, Herrera Estrella, et al., (1983) *Nature* 303: 209-213; Meijer, et al., (1991) *Plant Mol. Biol.* 16: 807-820; hygromycin, Waldron, et al., (1985) *Plant Mol. Biol.* 5: 103-108; Zhijian, et al., (1995) *Plant Science* 108: 219-227; streptomycin, Jones, et al., (1987) *Mol. Gen. Genet.* 210: 86-91; spectinomycin, Bretagne-Sagnard, et al., (1996) *Transgenic Res.* 5: 131-137; bleomycin, Hille, et al., (1990) *Plant Mol. Biol.* 7: 171-176; sulfonamide, Guerineau, et al., (1990) *Plant Mol. Biol.* 15: 127-136; bromoxynil, Stalker, et al., (1988) *Science* 242: 419-423; glyphosate, Shaw, et al., (1986) *Science* 233: 478-481; phosphinothricin, DeBlock, et al., (1987) *EMBO J.* 6: 2513-2518.

Further, when linking a root promoter of the invention with a nucleotide sequence encoding a detectable protein, expression of a linked sequence can be tracked in the root, thereby providing a useful so-called screenable or scorable markers. The expression of the linked protein can be detected without the necessity of destroying tissue. More recently, interest has increased in utilization of screenable or scorable markers. By way of example without limitation, the promoter can be linked with detectable markers including a β-glucuronidase, or uidA gene (GUS), which encodes an enzyme for which various chromogenic substrates are known (Jefferson, et al., (1986) *Proc. Natl. Acad. Sci. USA* 83: 8447-8451); chloramphenicol acetyl transferase; alkaline phosphatase; a R-locus gene, which encodes a product that regulates the production of anthocyanin pigments (red color) in plant tissues (Dellaporta, et al., (1988) in *Chromosome Structure and Function*, Kluwer Academic Publishers, Appels and Gustafson eds., pp. 263-282; Ludwig, et al., (1990) *Science* 247: 449); a p-lactamase gene (Sutcliffe, (1978) *Proc. Nat'l. Acad. Sci. U.S.A.* 75: 3737), which encodes an enzyme for which various chromogenic substrates are known (e.g., PADAC, a chromogenic cephalosporin); a xylE gene (Zukowsky, et al., (1983) *Proc. Nat'l. Acad. Sci. U.S.A.* 80: 1101), which encodes a catechol dioxygenase that can convert chromogenic catechols; an α-amylase gene (Ikuta, et al., (1990) *Biotech.* 8: 241); a tyrosinase gene (Katz, et al., (1983) *J. Gen. Microbiol.* 129: 2703), which encodes an enzyme capable of oxidizing tyrosine to DOPA and dopaquinone, which in turn condenses to form the easily detectable compound melanin a green fluorescent protein (GFP) gene (Sheen, et al., (1995) *Plant J.* 8(5): 777-84); a lux gene, which encodes a luciferase, the presence of which may be detected using, for example, X-ray film, scintillation counting, fluorescent spectrophotometry, low-light video cameras, photon counting cameras or multi-well luminometry (Teeri, et al., (1989) *EMBO J.* 8: 343); DS-RED EXPRESS (Matz, et al., (1999) *Nature Biotech.* 17:969-973, Bevis, et al., (2002) *Nature Biotech* 20: 83-87, Haas, et al., (1996) *Curr. Biol.* 6: 315-324); *Zoanthus* sp. yellow fluorescent protein (ZsYellow) that has been engineered for brighter fluorescence (Matz, et al., (1999) *Nature Biotech.* 17: 969-973, available from BD Biosciences Clontech, Palo Alto, Calif., USA, catalog no. K6100-1); and cyan florescent protein (CYP) (Bolte, et al., (2004) *J. Cell Science* 117: 943-54 and Kato, et al., (2002) *Plant Physiol* 129: 913-42).

A transformation vector comprising the particular regulatory sequences of the present invention, operably linked to an isolated nucleotide sequence of interest in an expression cassette, can be used to transform any plant. In this manner, genetically modified plants, plant cells, plant tissue, root, and the like can be obtained. Transformation protocols can vary depending on the type of plant or plant cell, i.e., monocot or dicot, targeted for transformation. Suitable methods of transforming plant cells include microinjection, Crossway, et al., (1986) *Biotechniques* 4: 320-334; electroporation, Riggs, et al., (1986) *Proc. Natl. Acad. Sci. USA* 83: 5602-5606; *Agrobacterium*-mediated transformation, see, for example, Townsend, et al., U.S. Pat. No. 5,563,055; direct gene transfer, Paszkowski, et al., (1984) *EMBO J.* 3: 2717-2722; and ballistic particle acceleration, see, for example, Sanford, et al., U.S. Pat. No. 4,945,050, Tomes, et al., (1995) in *Plant Cell, Tissue, and Organ Culture: Fundamental Methods*, ed. Gamborg and Phillips (Springer-Verlag, Berlin); and McCabe, et al., (1988) *Biotechnology* 6: 923-926. Also see, Weissinger, et al., (1988) *Annual Rev. Genet.* 22: 421-477; Sanford, et al., (1987) *Particulate Science and Technology* 5: 27-37 (onion); Christou, et al., (1988) *Plant Physiol.* 87: 671-674 (soybean); McCabe, et al., (1988) *Bio/Technology* 6: 923-926 (soybean); Datta, et al., (1990) *Bio/Technology* 8: 736-740 (rice); Klein, et al., (1988) *Proc. Natl. Acad. Sci. USA* 85: 4305-4309 (maize); Klein, et al., (1988) *Biotechnology* 6: 559-563 (maize); Klein, et al., (1988) *Plant Physiol.* 91: 440-444 (maize); Fromm, et al., (1990) *Biotechnology* 8: 833-839; Hooydaas-Van Slogteren, et al., (1984) *Nature* (London) 311: 763-764; Bytebier, et al., (1987) *Proc. Natl. Acad. Sci. USA* 84: 5345-5349 (Liliaceae); De Wet, et al., (1985) in *The Experimental Manipulation of Ovule Tissues*, ed. G. P. Chapman, et al., (Longman, New York), pp. 197-209 (pollen); Kaeppler, et al., (1990) *Plant Cell Reports* 9: 415-418; and Kaeppler, et al., (1992) *Theor. Appl. Genet.* 84: 560-566 (whisker-mediated transformation); D. Halluin, et al., (1992) *Plant Cell* 4:1495-1505 (electroporation); Li, et al., (1993) *Plant Cell Reports* 12:250-255 and Christou, et al., (1995) *Annals of Botany* 75:407-413 (rice); Osjoda, et al., (1996) *Nature Biotechnology* 14:745-750 (maize via *Agrobacterium tumefaciens*).

The cells that have been transformed can be grown into plants in accordance with conventional methods. See, for example, McCormick, et al., (1986) *Plant Cell Reports* 5: 81-84. These plants can then be grown and pollinated with the same transformed strain or different strains. The resulting plant having root-preferred expression of the desired phenotypic characteristic can then be identified. Two or more generations can be grown to ensure that root-preferred expression of the desired phenotypic characteristic is stably maintained and inherited.

The following examples are offered by way of illustration and not by way of limitation.

EXAMPLES

Regulatory regions from maize 6PGD were isolated from maize plants and cloned. Maize 6PGD was selected as a source of root-preferred regulatory elements based on the spatial and temporal expression of its products. The method for their isolation is described below.

Example 1

Prediction of Expression via Lynx MPSS

Lynx™ gene expression profiling technology was used to identify the maize 6PGD coding region as a candidate for promoter isolation. Massively parallel signature sequencing (MPSS, see, Brenner, et al., (2000) *Nature Biotechnology* 18: 630-634) indicated expression in various genotypes in root and other tissues, peaking at about 5486 ppm in root tissue. Results are summarized in FIG. 1. Expression was observed in a variety of maize tissues. MPSS data showed highest expression of maize 6PGD in root and kernel tissue.

Example 2

Prediction of Expression Pattern via RT PCR

RT-PCR was performed on maize roots from V2, V3, V4, V5, V6 and V8 stages, separated to thick crown roots and fine lateral roots, as well as pooled shoot tissue. Results as shown by gel electrophoresis agreed with the MPSS data. The RT-PCR data indicated expression at about V2 up to at least about V6. Signal was stronger in thicker crown root tissue compared to fine lateral roots, and highest expression was detected at around V5 stage.

Example 3

Isolation of Regulatory Sequences

Using the LYNX tag (GATCCAAGTCGAGTACT; SEQ ID NO: 5) and the ESTs containing the tag, a contig sequence was assembled which represented the maize 6PGD transcript. The promoter sequence was obtained by BLASTing the transcript sequence against a library of maize genes available from Iowa State University (called MAGI). This is a collection of maize sequences from the GSS (Genome Survey Sequence) where the overlapping sequences have been assembled into contigs. MAGI4_45584 was the top BLAST hit in the collection but contains only the 6PGD coding region. The next contig upstream is MAGI4_45583. This contig contained a significant region of upstream sequence and downstream sequence for 6PGD. By designing primers based on this sequence (forward primer—GGGTGAAAT-CAGTCGAACG (SEQ ID NO: 6); reverse primer—GTA-GACGGAGATCGGGAACC (SEQ ID NO: 7)), the promoter was amplified from B73 genomic DNA using PCR. A second PCR using nested primers (forward primer—GGCAAGCTTTTGGATGGGCACAAGATAGC (SEQ ID NO: 8); reverse primer—GGCAAGCTTGGTGGGTGGG-TAGGGTTT (SEQ ID NO: 9)) was carried out to generate the final promoter fragment. Additional sequence was added to the end of each primer to create restriction enzyme sites to facilitate cloning. Once amplified, the PCR fragments were sequenced and assembled into expression cassettes using the YFP coding region as the marker gene.

Example 4

Expression Data Using Promoter Sequences

Three promoter::YFP::terminator fusion constructs were prepared as set out below. The reference to "pinII" is the proteinase inhibitor II transcription terminator (An, et al., (1989) *Plant Cell* 1: 115-122). All vectors were constructed using standard molecular biology techniques (Sambrook, et al., supra).

ZM-6PGD PRO::YFP::PINII
ZM-6PGD TR1 PRO::YFP::PINII
ZM-6PGD TR2 PRO::YFP::PINII

Successful subcloning was confirmed by restriction analysis. Transformation and expression was confirmed as discussed infra.

TABLE 2

Summary of ZM-6PGD::YFP expression in transgenic maize plants.

| | Mature roots | Young roots | Leaves |
|---|---|---|---|
| T0 | Strong YFP expression | Moderate YFP expression | Trace expression |
| T1, V1-V4 stages | Strong YFP expression | Moderate YFP expression | No expression |
| T1, VR stage | Very weak expression | Weak expression | No expression |

Example 5

Transformation of Maize by Particle Bombardment

Preparation of Particles

Sixty mg of 0.6 u BioRad gold particles was weighed and placed in a 2 ml microfuge tube. 1 ml of 100% EtOH was added to the gold particles and sonicated briefly (Branson Sonifier Model 450, 40% output, constant duty cycle), the vortexed on high for 1 minute. The gold particles were pelleted by centrifugation at 10000 rpm (Biofuge) for one minute, and the EtOH was withdrawn. This EtOH wash was repeated two more times. After the last centrifugation, the 100% EtOH was withdrawn and replaced with 1 ml sterile deionized water and briefly sonicated. The solution was then aliquotted into 250 ul aliquots, and 750 ul of sterile deionized water was added to each aliquot.

Preparation of Particle-Plasmid DNA Association 100 ul of the tungsten particle (0.6 u gold particles) solution was briefly sonicated. 10 ul of plasmid DNA (100 ng/ul), 100 μl 2.5 M CaCl$_2$, and 10 μl 0.1 M spermidine was added and vortexed for 10 minutes at a medium speed.

After the association period, the tubes were centrifuged briefly, liquid removed, washed with 500 μl 100% ethanol by sonicating for 3 seconds, and centrifuging for 30 seconds. Again the liquid was removed, and 105 μl of 100% ethanol added to the final tungsten pellet. The associated particles/DNA were briefly sonicated and 10 μl spotted onto the center of each macro-carrier and allowed to dry ~2 minutes before bombardment.

Preparation of Target Seedling Roots

B73 seeds were placed along one edge of growth paper soaked in water. An additional piece of growth paper identical in size to the first was also soaked in water and overlaid onto the seeds. The growth paper—seed—growth paper sandwich was subsequently jelly rolled with the seed edge at the top of the roll. The roll was directionally placed into a beaker of water with the seeds at the top to allow for straight root growth. Seeds were allowed to germinate and develop for 2-3 days in the dark at 28° C. Prior to bombardment the outer skin layer of the cotyledon was removed and seedlings were placed in a sterile petri dish (60 mm) on a layer of Whatman #1 filter paper moistened with 1 mL of water. Two seedlings per plate were arranged in opposite orientations and anchored to the filter paper with a 0.5% agarose solution. 2-3 cm root tip sections were also excised from seedlings and arranged lengthwise in the plates for bombardment.

Particle Bombardment

To effect particle bombardment of root of kernels, the particle-DNA agglomerates were accelerated using a DuPont PDS-1000 particle acceleration device. The particle-DNA agglomeration was briefly sonicated and 10 μl were deposited on macrocarriers and the ethanol allowed to evaporate. The macrocarrier was accelerated onto a stainless-steel stopping screen by the rupture of a polymer diaphragm (rupture disk). Rupture is effected by pressurized helium. The velocity of particle-DNA acceleration is determined based on the rupture disk breaking pressure. A rupture disk pressure of 1100 psi was used.

The shelf containing the plate with the 12 DAP kernels was placed 5.1 cm below the bottom of the macrocarrier platform (shelf #3). To effect particle bombardment of the kernels, a rupture disk and a macrocarrier with dried particle-DNA agglomerates were installed in the device. The He pressure delivered to the device was adjusted to 200 psi above the rupture disk breaking pressure. A Petri dish with the target kernels was placed into the vacuum chamber and located in the projected path of accelerated particles. A vacuum was created in the chamber, preferably about 28 in Hg. After operation of the device, the vacuum was released and the Petri dish removed.

Bombarded kernels were analyzed for expression 18-24 hours after bombardment. Ability of the 6PGD promoter to drive expression in maize root from 2-3 days after germination was confirmed by GUS detection in of root of bombarded kernels. Strong signal in root was microscopically visualized. Expression was particularly noted in root tissue and no signal was observed in negative controls. The GUS expression was detectable in root of all samples examined and no background expression noted.

Example 7

Transformation and Regeneration of Maize Callus via *Agrobacterium*

Constructs used were as those set forth supra for microprojectile bombardment, except that the control was not employed in this experiment and the selectable marker for maize-optimized PAT (phosphinothricin acetyl transferase) was also included.

Preparation of *Agrobacterium* Suspension

*Agrobacterium* was streaked out from a −80° frozen aliquot onto a plate containing PHI-L medium and was cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) was added to a concentration of 50 mg/l in sterile ddH2O (stock solution A: K2HPO4 60.0 g/l, NaH2PO4 20.0 g/l, adjust pH to 7.0 w/KOH and autoclaved; stock solution B: NH4Cl 20.0 g/l, MgSO4.7H2O 6.0 g/l, KCl 3.0 g/l, CaCl2 0.20 g/l, FeSO4.7H2O 50.0 mg/l, autoclaved; stock solution C: glucose 5.56 g/l, agar 16.67 g/l (#A-7049, Sigma Chemicals, St. Louis, Mo.) and was autoclaved).

The plate can be stored at 4° C. and used usually for about 1 month. A single colony was picked from the master plate and was streaked onto a plate containing PHI-M medium [yeast extract (Difco) 5.0 g/l; peptone (Difco) 10.0 g/l; NaCl 5.0 g/l; agar (Difco) 15.0 g/l; pH 6.8, containing 50 mg/L spectinomycin] and was incubated at 28° C. in the dark for 2 days.

Five ml of either PHI-A, [CHU(N6) basal salts (Sigma C-1416) 4.0 g/l, Eriksson's vitamin mix (1000X, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1 g/l; 2,4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy-4'-hydroxyacetophenone, Aldrich chemicals) was added to a 14 ml Falcon tube in a hood. About 3 full loops (5 mm loop size) *Agrobacterium* was collected from the plate and suspended in the tube, then the tube vortexed to make an even suspension. One ml of the suspension was transferred to a spectrophotometer tube and the OD of the suspension is adjusted to 0.72 at 550 nm by adding either more *Agrobacterium* or more of the same suspension medium, for an *Agrobacterium* concentration of approximately 0.5×109 cfu/ml to 1×109 cfu/ml. The final *Agrobacterium* suspension was aliquoted into 2 ml microcentrifuge tubes, each containing 1 ml of the suspension. The suspensions were then used as soon as possible.

Embryo Isolation, Infection and Co-cultivation

About 2 ml of the same medium (here PHI-A or PHI-I) which is used for the *Agrobacterium* suspension was added into a 2 ml microcentrifuge tube. Immature embryos were isolated from a sterilized ear with a sterile spatula (Baxter Scientific Products S1565) and dropped directly into the medium in the tube. A total of about 100 embryos are placed in the tube. The optimal size of the embryos was about 1.0-1.2 mm. The cap was then closed on the tube and the tube vortexed with a Vortex Mixer (Baxter Scientific Products S8223-1) for 5 sec. at maximum speed. The medium was removed and 2 ml of fresh medium were added and the vortexing repeated. All of the medium was drawn off and 1 ml of *Agrobacterium* suspension was added to the embryos and the tube is vortexed for 30 sec. The tube was allowed to stand for 5 min. in the hood. The suspension of *Agrobacterium* and embryos was poured into a Petri plate containing either PHI-B medium [CHU(N6) basal salts (Sigma C-1416) 4.0 g/l; Eriksson's vitamin mix (1000×, Sigma-1511) 1.0 ml/l; thiamine.HCl 0.5 mg/l; 2,4-D1.5 mg/l; L-proline 0.69 g/l; silver nitrate 0.85 mg/l; gelrite (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2, 4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system. Any embryos left in the tube were transferred to the plate using a sterile spatula. The *Agrobacterium* suspension was drawn off and the embryos placed axis side down on the media. The plate was sealed with Parafilm tape or Pylon Vegetative Combine Tape (product named "E.G.CUT" and is available in 18 mm×50 m sections; Kyowa Ltd., Japan) and was incubated in the dark at 23-25° C. for about 3 days of co-cultivation.

Resting, Selection and Regeneration Steps

For the resting step, all of the embryos were transferred to a new plate containing PHI—C medium [CHU(N6) basal salts (Sigma C-1416) 4.0 g/l; Eriksson's vitamin mix (1000× Sigma-1511) 1.0 ml/l; thiamine.HCl 0.5 mg/l; 2,4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm or Pylon tape and incubated in the dark at 28° C. for 3-5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation For selection, all of the embryos were then transferred from the PHI-C medium to new plates containing PHI-D medium, as a selection medium, [CHU(N6) basal salts (SIGMA C-1416) 4.0 g/l; Eriksson's vitamin mix (1000X, Sigma-1511) 1.0 ml/l; thiamine.HCl 0.5 mg/l; 2,4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K.K., Tokyo, Japan) 1.5 mg/l for the first two weeks followed by 3 mg/l for the remainder of the time; pH 5.8] putting about 20 embryos onto each plate.

The plates were sealed as described above and incubated in the dark at 28° C. for the first two weeks of selection. The embryos were transferred to fresh selection medium at two-week intervals. The tissue was subcultured by transferring to fresh selection medium for a total of about 2 months. The herbicide-resistant calli are then "bulked up" by growing on the same medium for another two weeks until the diameter of the calli is about 1.5-2 cm.

For regeneration, the calli were then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in the dark at 28° C. for 1-3 weeks to allow somatic embryos to mature. The calli were then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; gelrite 1.5 g/l; pH 5.6] at 25° C. under a daylight schedule of 16 hrs. light (270 uE m-2 sec-1) and 8 hrs. dark until shoots and roots are developed. Each small plantlet was then transferred to a 25×150 mm tube containing PHI-F medium and is grown under the same conditions for approximately another week. The plants were transplanted to pots with soil mixture in a greenhouse. DS-RED EXPRESS events are determined at the callus stage or regenerated plant stage.

Ability of the 6PGD promoter and truncated variant to drive expression in maize root from 10-40 DAP was confirmed by DS-RED EXPRESS detection in plant root tissue by the procedures outlined supra. In the 1.2 kb version of the promoter, preferred root expression was observed, along with low levels of expression in pollen. In the 0.8 and 0.6 versions of the promoter, root preferred expression was observed, with no expression observed in pollen.

Example 8

Construction of Promoter Variant

Figure 3:
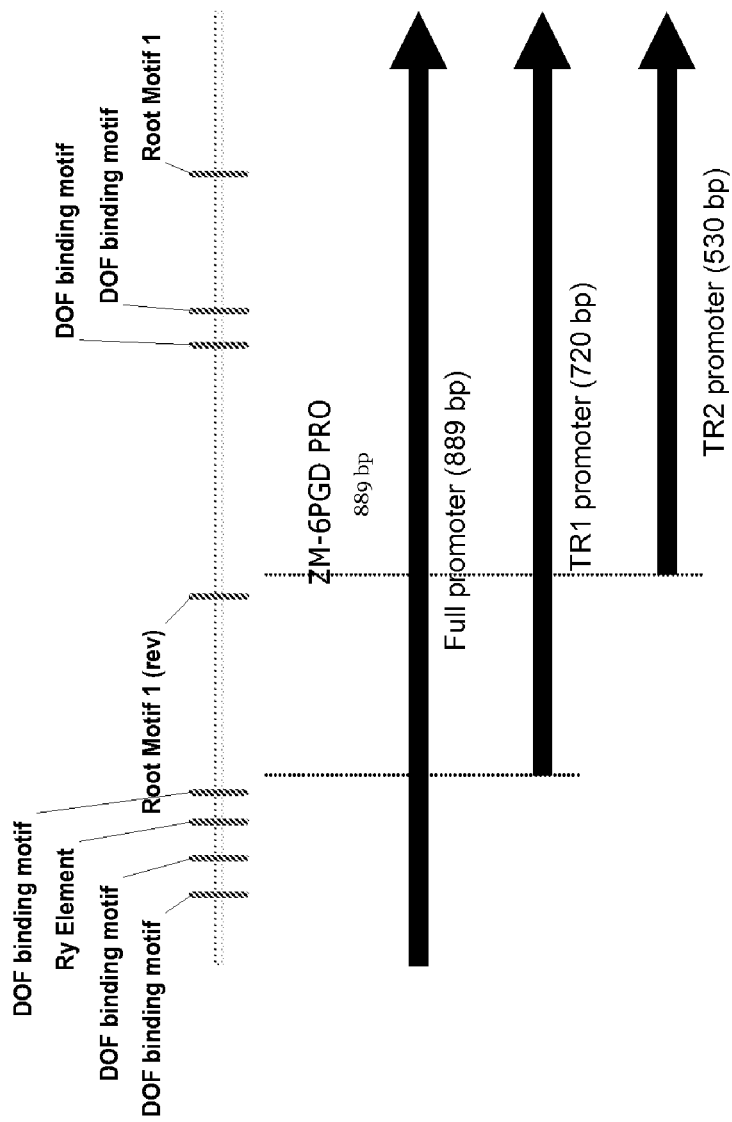
FIG. 3. Diagrammed illustration of the two variants of the promoter by truncations. TR1 (truncated 1) (SEQ ID NO: 10) promoter was obtained by removing 169 bp from the 5'-end of the full promoter. TR2 (truncated 2) (SEQ ID NO: 11) promoter was generated through further truncating 190 bp from the 5'-end of TR1 promoter. The positions of the truncations relative to the putative cis-elements of the full promoter are shown with vertical dotted lines.

Deletion variants are made by truncating the promoter sequence from 5'-end at two positions in the promoter region, with the deletions shown in FIG. 3. The truncations resulted in two promoter variants—one is 720 nucleotides (ZM-6PGD TR1 PRO) and the other 530 nucleotides (ZM-6PGD TR2 PRO) in length. FIG. 3 also indicates correspondence of each deletion with the motifs of Table 1.

Constructs are prepared as in Example 4, using the truncated variant, linked with the YFP marker and PINII terminator region. Successful subcloning is confirmed by restriction analysis. Transformation of seedling roots is carried out using the microprojectile bombardment method set out above.

Although the foregoing invention has been described in some detail by way of illustration and example for purposes of clarity of understanding, it will be obvious that certain changes and modifications may be practiced within the scope of the appended claims. All references cited are incorporated herein by reference.

That which is claimed:

1. An isolated nucleic acid molecule comprising a polynucleotide which initiates transcription in a plant cell and comprises a sequence selected from the group consisting of:
   a) the sequence of SEQ ID NO: 2; and
   b) the sequence which is the full-length complement of SEQ ID NO: 2.

2. An expression cassette comprising the nucleic acid molecule of claim 1 operably linked to a polynucleotide of interest.

3. A vector comprising the expression cassette of claim 2.

4. A plant cell having stably incorporated into its genome the expression cassette of claim 2.

5. The plant cell of claim 4, wherein said plant cell is from a monocot.

6. The plant cell of claim 5, wherein said monocot is maize, barley, wheat, oat, rye, sorghum or rice.

7. A plant having stably incorporated into its genome the expression cassette of claim 2.

8. The plant of claim 7, wherein said plant is a monocot.

9. The plant of claim 8, wherein said monocot is maize, barley, wheat, oat, rye, sorghum or rice.

10. A transgenic seed of the plant of claim 7.

11. The plant of claim 7, wherein the polynucleotide of interest encodes a gene product that confers pathogen or insect resistance.

12. A plant transformed with the expression cassette of claim 2, where said polynucleotide of interest encodes a polypeptide involved in nitrogen use efficiency, drought tolerance, root lodging resistance, corn root worm resistance, carbohydrate metabolism, protein metabolism, fatty acid metabolism, or phytohormone biosynthesis.

* * * * *

SEQUENCE LISTING

```
<160> NUMBER OF SEQ ID NOS: 11

<210> SEQ ID NO 1
<211> LENGTH: 2655
<212> TYPE: DNA
<213> ORGANISM: Zea mays
<220> FEATURE:
<221> NAME/KEY: misc_feature
<222> LOCATION: 333
<223> OTHER INFORMATION: n = A,T,C or G

<400> SEQUENCE: 1
ttggatgggc acaagatagc gatttgctgt ggcgttttag ttgttgttgc tgtgctgggg      60
gcagaaagtc tagtgccgtg cttgacgaag acggggtcaa agcgcttgca gcgacgatgt     120
acgatttgga gccatgcaac tagctcgtca gcattactct aaagtaatac tgcaactgca     180
gtcagttgag ctcgaagacg ctgagagagt aataggatac cattagcctt tccgtcgctc     240
ctagtacttg gctttctgtg gagaatcgga gctttattat agcaatcatc aaaacgaagt     300
tgggtacgta cttgggttca tagtcttctc cancatgttc agcgaatatg acttctggcc     360
ggcttcgagg gatggggatg cagcacgcac gggcacggcc gttggttgcc aagggccgag     420
ccttgtaggg gtcggagaac acgagctttg ttggttggtc gcgcgcgccg agcggcagct     480
ggcccttgga ctgatcgacc ggccaagcct gtgccgtttg gccgcctcga tgagtccgcc     540
tcaccgcgag gcagccagca gcaggcggct gcggccgcga aagaacgcaa gagtgaggtg     600 gcccttgca gaaagcacct caagtcctct ggaatttttg cttccatgag cgtcgggtgt     660
accggatcca ctctattcct aggacagttt ctacgataac cccagactcc agggacccca     720
tccaaaaccc cgggccgcaa tatttctatc ccctacaggc tacagcactg tccaccttca     780
cttccgtccg ttccccgaa ctctctctct cctcctcggc cacctcccat ccccgttcct     840 tccctccat ctcatcaccg ccgccagcgc caaaaccta cccacccacc caccgatggc     900
ctccccggcg ccggcgtccc ccgcggccgc ggcggcgcac tgcccccgc cgcgcatcgg     960
```

```
gctcgcgggc ctcgccacca tgggccagaa cctggccctg aacatcgccg agaaagggtt    1020
cccgatctcc gtctacaacc gcaccgccgc caaggtggac tccacgctgt cccgcgcgcg    1080
ggacgagggc tcgctgccgg tgctgggcca ccgcgacccg cgcggttcg tgctgtccct     1140 cgcgcgcccg cgcgccgtcg tgctgctcgt ccaggccggc cccgccgtcg acgccaccat    1200
ccaggccctc tccccctacc tcgagcccgg ggacgccatc gtcgacggcg caacgagtg     1260 gtaccagaac acggagcgcc gcatccagga ggcggcggcg cgcggcgtcc tgtacctcgg    1320
gatgggcgtc tccggcggcg aggagggcgc gcggaacggg ccctcgctca tgcccggcgg    1380
cagcgccgac gcctacgcca acatcaggga catcctccag aaggccgccg cgcagacgga    1440
ggacggcgcg tgcgtcacct cgtcgggcc cggcggcgcc ggcaacttcg tcaagatggt     1500
gcacaacggg atcgagtacg gcgacatgca gctcatcgcc gaggcgtacg acgtgctccg    1560
caggctcggg ggcctgtcca actccgagat cgcgcgacgtc ttcgcggact ggaacagggg   1620
ggagctcgag agcttcctgg tccagatcac cgccgacatt ttcaccgtgg ctgacccgtt    1680
ggacgggagc ggcgccggcg gggcgctggt tgacaggatt ctggacaaga ctgggatgaa    1740
ggggaccggg aaatggaccg tgcagcaggc ggcggagctt gcggtggcag cgcccacgat    1800
tgccgcgtcg ctggacggga ggtacctctc agggttgaag gaccaacggg tcgcagccgc    1860
tggggtgctg gaggaagagg ggatgccggc gggcctgttg agaccgttaa atgtcgacaa    1920
gaaggtgctg gtggataggg tcaggcaagc gctctacgcc tccaagattt gcagctatgc    1980
gcagggcatg aatctgctgc gagccaagag cgtggagaag ggatggaacc ttaacctcgc    2040
agagcttgcc aggatctgga agggcggctg cattatccgt gcgaggttcc ttgataggat    2100
caagagcgcg tacgacagga atcctgagct cgccaatttg attgttgaca gagagtttgc    2160
aagggagatg gtgcagcggc agaacgcgtg gaggtgggtt gtggcacgcg cggtggaggc    2220
tggcattagc acgccaggaa tgactgctag cctttcgtac ttcgatacct acagatcaag    2280
tcgattgcct gcaaatctga tccaagcgca gagggatctg tttggtgcac acacctatga    2340
gcgcattgac tgtccggggtt cattccacac cgaatggacc aagctggcga ggaggagcaa    2400
tggcgcagcc atttgaggaa ttggttggta tgagaaggga tgttttctgc tttgtgtgat    2460
ttctctctgt gggttatctt ttgttttact attgttatct ttatgcttct agatccaagt    2520
cgagtacttc aaataatgct gtactgtatg gttggcaagt gaagaacatt gtgtagcttc    2580
agttttactg tgatgtaggt acacacagtt tgattctctt aattttggta tgcaattgct    2640
atgatgcctc acaaa                                                    2655

<210> SEQ ID NO 2
<211> LENGTH: 889
<212> TYPE: DNA
<213> ORGANISM: Zea mays
<220> FEATURE:
<221> NAME/KEY: misc_feature
<222> LOCATION: 333
<223> OTHER INFORMATION: n = A,T,C or G

<400> SEQUENCE: 2
ttggatgggc acaagatagc gatttgctgt ggcgttttag ttgttgttgc tgtgctgggg      60
gcagaaagtc tagtgccgtg cttgacgaag acggggtcaa agcgcttgca gcgacgatgt     120
acgatttgga gccatgcaac tagctcgtca gcattactct aaagtaatac tgcaactgca     180
gtcagttgag ctcgaagacg ctgagagagt aataggatac cattagcctt tccgtcgctc     240
```

```
ctagtacttg gctttctgtg gagaatcgga gctttattat agcaatcatc aaaacgaagt      300
tgggtacgta cttgggttca tagtcttctc cancatgttc agcgaatatg acttctggcc      360
ggcttcgagg gatggggatg cagcacgcac gggcacggcc gttggttgcc aagggccgag      420
ccttgtaggg gtcggagaac acgagctttg ttggttggtc gcgcgcgccg agcggcagct      480
ggcccttgga ctgatcgacc ggccaagcct gtgccgtttg gccgcctcga tgagtccgcc      540
tcaccgcgag gcagccagca gcaggcggct gcggccgcga aagaacgcaa gagtgaggtg      600
gccctttgca gaaagcacct caagtcctct ggaatttttg cttccatgag cgtcgggtgt      660
accgGatcca ctctattcct aggacagttt ctacgataac cccagactcc agggacccca      720
tccaaaaccc cgggccgcaa tatttctatc ccctacaggc tacagcactg tccaccttca      780
cttccgtccg ttccccgaa ctctctctct cctcctcggc cacctcccat ccccgttcct      840
tcccctccat ctcatcaccg ccgccagcgc caaaaccta cccacccac                  889

<210> SEQ ID NO 3
<211> LENGTH: 1899
<212> TYPE: DNA
<213> ORGANISM: Zea mays

<400> SEQUENCE: 3 gttccccga actctctctc tcctcctcgg ccacctccca tccccgttcc ttcccctcca       60
tctcatcacc gccgccagcg ccaaaaccct acccacccac ccaccgatgg cctccccggc      120
gccggcgtcc cccgcggccg cggcggcgca ctgcccccg ccgcgcatcg ggctcgcggg      180
cctcgccacc atgggccaga acctggccct gaacatcgcc gagaaagggt tcccgatctc      240
cgtctacaac cgcaccgccg ccaaggtgga ctccacgctg tcccgcgcgc gggacgaggg      300
ctcgctgccg gtgctgggcc accgcgaccc gcgcgggttc gtgctgtccc tcgcgcgccc      360
gcgcgccgtc gtgctgctcg tccaggccgg ccccgccgtc gacgccacca tccaggccct      420
ctcccccctac ctcgagcccg ggacgccat cgtcgacggc ggcaacgagt ggtaccagaa      480
cacggagcgc cgcatccagg aggcggcggc gcgcggcgtc ctgtacctcg ggatgggcgt      540
ctccggcggc gaggagggcg cgcggaacgg gccctcgctc atgcccggcg cagcgccga       600
cgcctacgcc aacatcaggg acatcctcca aaggccgcc gcgcagacgg aggacggcgc      660
ctgcgtcacc ttcgtcgggc ccggcggcgc cggcaacttc gtcaagatgg tgcacaacgg      720
gatcgagtac ggcgacatgc agctcatcgc cgaggcgtac gacgtgctcc gcaggctcgg      780
gggcctgtcc aactccgaga tcgccgacgt cttcgcggac tggaacaggg gggagctcga      840
gagcttcctg gtccagatca ccgccgacat tttccaccgtg gctgacccgt tggacgggag      900
cggcgccggc ggggcgctgg ttgacaggat tctggacaag actgggatga aggggaccgg      960
gaaatggacc gtgcagcagg cggcggagct tgcggtggca gcgccacga ttgccgcgtc     1020
gctgacgggg aggtacctct cagggttgaa ggaccaacgg gtcgcagccg ctggggtgct     1080
ggaggaagag gggatgccgg cgggcctgtt ggagaccgtt aatgtcgaca agaaggtgct     1140
ggtggatagg gtcaggcaag cgctctacgc ctccaagatt tgcagctatg cgcagggcat     1200
gaatctgctg cgagccaaga gcgtggagaa gggatggaac cttaacctcg cagagcttgc     1260
caggatctgg aagggcggct gcattatccg tgcgaggttc cttgataggg tcaagagcgc     1320
gtacgacagg aatcctgagc tcgccaattt gattgttgac agagagtttg caagggagat     1380
ggtgcagcgg cagaacgcgt ggaggtgggt tgtggcacgc gcggtggagg ctggcattag     1440
cacgccagga atgactgcta gcctttcgta cttcgatacc tacagatcaa gtcgattgcc     1500
```

```
tgcaaatctg atccaagcgc agagggatct gtttggtgca cacacctatg agcgcattga    1560
ctgtccgggt tcattccaca ccgaatggac caagctggcg aggaggagca atggcgcagc    1620
catttgagga attggttggt atgagaaggg atgttttctg ctttgtgtga tttctctctg    1680
tgggttatct tttgttttac tattgttatc tttatgcttc tagatccaag tcgagtactt    1740
caaataatgc tgtactgtat ggttggcaag tgaagaacat tgtgtagctt cagttttact    1800
gtgatgtagg tacacacagt ttgattctct taattttggt atgcaattgc tatgatgcct    1860
cacaaaaaaa aaaaaaaaaa aaaaaaaaaa aaaaaaaa                             1899

<210> SEQ ID NO 4
<211> LENGTH: 239
<212> TYPE: DNA
<213> ORGANISM: Zea mays

<400> SEQUENCE: 4
ggaattggtt ggtatgagaa gggatgtttt ctgctttgtg tgatttctct ctgtgggtta     60
tcttttgttt tactattgtt atctttatgc ttctagatcc aagtcgagta cttcaaataa    120
tgctgtactg tatggttggc aagtgaagaa cattgtgtag cttcagtttt actgtgatgt    180
aggtacacac agtttgattc tcttaatttt ggtatgcaat tgctatgatg cctcacaaa     239

<210> SEQ ID NO 5
<211> LENGTH: 17
<212> TYPE: DNA
<213> ORGANISM: Artificial Sequence
<220> FEATURE:
<223> OTHER INFORMATION: oligonucleotide

<400> SEQUENCE: 5
gatccaagtc gagtact                                                    17

<210> SEQ ID NO 6
<211> LENGTH: 19
<212> TYPE: DNA
<213> ORGANISM: Artificial Sequence
<220> FEATURE:
<223> OTHER INFORMATION: primenr

<400> SEQUENCE: 6
gggtgaaatc agtcgaacg                                                  19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gtagacggag atcgggaacc                                                 20

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
ggcaagcttt tggatgggca caagatagc                                       29
```

```
<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
ggcaagcttg gtgggtgggt agggttt                                             27

<210> SEQ ID NO 10
<211> LENGTH: 720
<212> TYPE: DNA
<213> ORGANISM: Zea mays

<400> SEQUENCE: 10
ctgcaactgc agtcagttga gctcgaagac gctgagagag taataggata ccattagcct         60
ttccgtcgct cctagtactt ggctttctgt ggagaatcgg agctttatta tagcaatcat        120
caaaacgaag ttgggtacgt acttgggttc atagtcttct ccacatgttc agcgaatatg        180
acttctggcc ggcttcgagg gatggggatg cagcacgcac gggcacggcc gttggttgcc        240
aagggccgag ccttgtaggg gtcggagaac acgagctttg ttggttggtc gcgcgcgccg        300
agcggcagct ggcccttgga ctgatcgacc ggccaagcct gtgccgtttg ccgcctcga         360 tgagtccgcc tcaccgcgag gcagccagca gcaggcggct gcggccgcga agaacgcaa         420 gagtgaggtg gcccttttgca gaaagcacct caagtcctct ggaattttg cttccatgag       480 cgtcgggtgt accggatcca ctctattcct aggacagttt ctacgataac cccagactcc        540
agggacccca tccaaaaccc cgggccgcaa tatttctatc cctacaggc tacagcactg         600 tccaccttca cttccgtccg ttcccccgaa ctctctctct cctcctcggc cacctcccat        660
ccccgttcct tcccctccat ctcatcaccg ccgccagcgc caaaaccta cccacccacc         720

<210> SEQ ID NO 11
<211> LENGTH: 530
<212> TYPE: DNA
<213> ORGANISM: Zea mays

<400> SEQUENCE: 11
ggcttcgagg gatggggatg cagcacgcac gggcacggcc gttggttgcc aagggccgag         60
ccttgtaggg gtcggagaac acgagctttg ttggttggtc gcgcgcgccg agcggcagct        120
ggcccttgga ctgatcgacc ggccaagcct gtgccgtttg ccgcctcga tgagtccgcc         180 tcaccgcgag gcagccagca gcaggcggct gcggccgcga agaacgcaa gagtgaggtg        240 gcccttttgca gaaagcacct caagtcctct ggaattttg cttccatgag cgtcgggtgt       300
accggatcca ctctattcct aggacagttt ctacgataac cccagactcc agggacccca       360
tccaaaaccc cgggccgcaa tatttctatc cctacaggc tacagcactg tccaccttca        420
cttccgtccg ttcccccgaa ctctctctct cctcctcggc cacctcccat ccccgttcct       480
tcccctccat ctcatcaccg ccgccagcgc caaaaccta cccacccacc                   530
```